US 6,683,784 B1
(12) United States Patent
Bidwell et al.

(10) Patent No.: US 6,683,784 B1
(45) Date of Patent: Jan. 27, 2004

(54) ERGONOMIC DATA SYSTEM STAND

(75) Inventors: Dean Jeffrey Bidwell, Everett, WA (US); Andrew Lyle Walston, Seattle, WA (US); Stephen Bruce Hooper, Redmond, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 09/964,014

(22) Filed: Sep. 25, 2001

Related U.S. Application Data

(60) Provisional application No. 60/252,992, filed on Nov. 22, 2000.

(51) Int. Cl.$^7$ ................................................. G06F 1/16
(52) U.S. Cl. ...................... 361/679; 361/724; 248/122.1
(58) Field of Search ................................. 361/679, 724; 248/123.11, 122.1, 124.1, 280.11; D6/429; 312/223.2, 223.3; 600/437

(56) References Cited

U.S. PATENT DOCUMENTS

| | | | |
|---|---|---|---|
| 5,544,449 A | | 8/1996 | Amelio et al. |
| 5,672,088 A | | 9/1997 | Chininis |
| 5,715,566 A | | 2/1998 | Weaver et al. |
| 5,913,582 A | * | 6/1999 | Coonan .................... 312/223.3 |
| 6,098,936 A | * | 8/2000 | Birrell ...................... 248/122.1 |
| 6,175,991 B1 | | 1/2001 | Driesman et al. |
| 6,394,402 B2 | * | 5/2002 | Coonan et al. ......... 248/123.11 |
| 6,447,451 B1 | * | 9/2002 | Wing et al. ................. 600/437 |
| 6,493,220 B1 | * | 12/2002 | Clark et al. ................. 361/686 |

OTHER PUBLICATIONS

"Kretz Museum Tour–The History of Ultrasound", F. Wiesauer, Kretz Technik in Austria, interviewed by Roberta Speyer, http://www.obgyn.net/avtranscripts/rsna/rsna2000_kretzmuseum.htm.*
Kretztechnik AG; Combison 330.
ATL Ultrasound; HDI 5000; 1997.
Siemens Medical Systems, Inc.; SONOLINE Versa Plus Imaging System, 1998.
Siemens Medical Systems, Inc.; SONOLINE Adara; 1999.
Siemens Medical Systems, Inc.; SONOLINE Omnia; 2000.
Siemens Medical Systems, Inc.; SONOLINE Elegra; 2001.

* cited by examiner

Primary Examiner—Darren Schuberg
Assistant Examiner—Anthony Q. Edwards (57) ABSTRACT

A particular orientation of a control panel and an accessory device provides ergonomic benefits to an operator. A user control is mounted on a corner of the stand. The user interface of an accessory device is mounted at about a 45° angle to the control panel on one side of the stand. User tools, such as a transducer connector, are also mounted at about a 45° angle to the control panel, such as mounted on a different side of the stand adjacent to the control panel. Convenient access is provided to all of the control panel, the user interface of the accessory device, and the user tools. Additional leg room is also provided due to the angle of the stand relative to the user position in front of the control panel. The ultrasound system or other data system with this orientation of components allows ergonomic use of the system in a more confined space.

27 Claims, 4 Drawing Sheets

FIG. 6

ERGONOMIC DATA SYSTEM STAND

This application claims the benefit of provisional application Ser. No. 60/252,992 filed Nov. 22, 2000.

BACKGROUND

This present invention relates to stands for data systems. In particular, ergonomic stands for data systems, such as ultrasound systems, are provided.

Ultrasound systems include a cube-shaped housing for storing electrical components of the ultrasound system. A control panel or keyboard extends from one of the four sides of the housing. A display is provided on top of the housing.

In addition to the control panel, a user interacts with transducers and user interfaces on accessory devices, such as VCRs or printers. The user needs easy access to the control panel, the accessory's user interface, and the transducer connections, but all three cannot fit in the same location. The control panel is typically positioned to provide the easiest access to the user. The transducers typically are located at a next-easiest-to-access location, such as below the control panel or on a side of the stand adjacent to the control panel. The user interfaces of accessory devices are positioned in a least desirable position comparatively, such as on a side of the stand opposite to the transducers or below the control panel or even on top of the display monitor.

Ultrasound systems are typically used in a constrained environment, such as a small room with a bed and other medical equipment. Such confined environments may make it difficult for a user to reach around to the side of the ultrasound stand or below a control panel. The user's knees or feet may be blocked or contacted by the ultrasound system stand, hurting the user or accidentally activating controls.

BRIEF SUMMARY

The present invention is defined by the following claims, and nothing in this section should be taken as a limitation on those claims. By way of introduction, the preferred embodiments described below include a method and stands for operating a data system. The control panel of the data system is oriented at more than 10° and less than 80° to the user interface of an accessory device.

In an ultrasound data system embodiment, the user control is mounted on a corner of the stand. The user interface of an accessory device is mounted at about a 45° angle to the control panel on one side of the stand. User tools, such as a transducer connector, are also mounted at about a 45° angle to the control panel, such as mounted on a different side of the stand adjacent to the control panel. Convenient access is provided to all of the control panel, the user interface of the accessory device, and the user tools. Additional leg room is also provided due to the angle of the stand relative to the user position in front of the control panel. The ultrasound system or other data system with this orientation of components allows ergonomic use of the system in a more confined space.

In a first aspect, a movable stand for operating a data system is provided. A control panel connects with the stand. An accessory device with a user interface also connects with the stand. The control panel is oriented at more than 10° and less than 80° to the user interface of the accessory device. The orientation is relative to an operator position.

In a second aspect, a stand for operating a data system is provided. A control panel and an output device having an output port connects with the stand. The control panel is oriented at more than 10° and less than 80° to the output port, the orientation relative to an operator position.

In a third aspect, an ultrasound system stand for use with an ultrasound system is provided. An ultrasound system connects with the stand. A control panel and an accessory device having a user interface also connect with the stand and operatively connect with the ultrasound system. The control panel is oriented at more than 10° and less than 80° to the user interface of the accessory device, the orientation relative to an operator position.

In a fourth aspect, a method for ergonomically connecting ultrasound system components is provided. The method includes the acts of: (a) connecting a user interface of an accessory device with an ultrasound system stand; (b) connecting a control panel to the ultrasound system stand; (c) orienting the control panel at more than 10° and less than 80° to the user interface of the accessory device relative to an operator position; (d) connecting a transducer connector with the ultrasound system stand; and (e) orienting the control panel at more than 10° and less than 80° to the transducer connector relative to the operator position, the transducer connector spaced 90° to 270° around the diameter of the ultrasound system stand from the user interface of the accessory device.

Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different view.

DETAILED DESCRIPTION OF THE PREFERRED EMBODIMENTS

Simultaneous visual and physical access is provided to a control panel, a user interface or output port of an accessory or output device, and any user tools associated with a data system. The orientation of the control panel at an acute angle to adjacent sides of a data system stand provides the simultaneous visual and physical access. For example, by angling the orientations of the accessory device and any user tools at about 45° relative to the user, the user can access the various components without moving away from the data system. The control panel is connected at a corner of the stand for efficient access while reducing interference with the user's knees and feet.

Figures 1A, 1B:
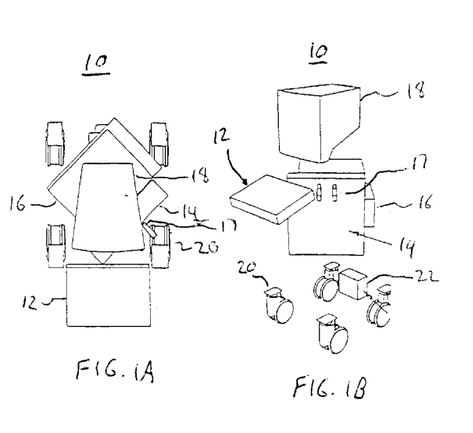
FIGS. 1A, 1B sand 1C are top, right perspective and left perspective views of one embodiment of part of a data system stand.
Figure 1C:
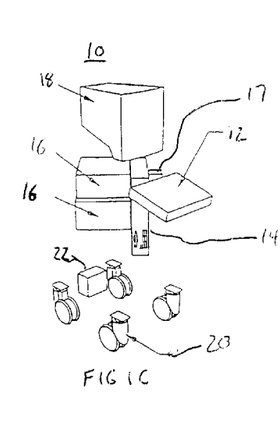

FIGS. 1A–C show top, right perspective and left perspective views of components connected with or forming part of a data system stand 10. The stand 10 includes a control panel 12, a data system 14, an accessory device 16, an optional user tool mount 17, a display 18, one or more wheels or casters 20, and a transformer 22. Fewer, different or additional components may be included. In one embodiment, the data system stand 10 comprises an ultrasound system stand. Other data systems may be provided, such as a computer workstation, medical imaging workstation, materials testing station, ticketing station or other processing systems.

The components of the data system stand 10 listed above are connected through a framework or housing structure. The framework or housing structure comprises plastic, wood, metal, fiberglass and combinations thereof. The framework and/or housing material is of sufficient strength to support and prevent damage to any of the various components of the data system stand 10. This structure rigidly and stably connects the wheels or casters 20 to one another. Preferably, the transformer 22 is included within this structure between the wheels or casters 20 and sufficiently high to provide clearance when rolling. This structure rigidly and stably extends upward preferably along one side above a pair of adjacent wheels. The control panel 12, data system 14, accessory device 16, optional user tool mount 17, and display 18 are mounted to the upward extension of the rigid structure. The housing and/or framework is of any shape for holding the components.

The control panel 12 comprises a housing with a keyboard, a track ball, a touch pad, membrane or push button keys, slides, other user input devices now known or later developed, and combinations thereof. In one embodiment, a qwerty keyboard, dedicated keys, a plurality of slides, and a track ball are provided for controlling an ultrasound system. The control panel 12 houses the user input devices in a cube or rectangular housing. In alternative embodiments, housings with other geometrical shapes, such as circular, rounded, semi-circular, multi-sided and combinations thereof, are provided.

Figure 2:
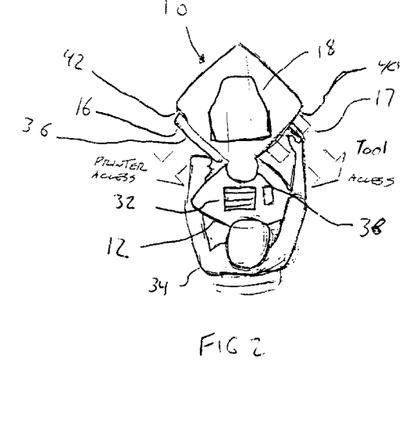
FIG. 2 is a top view of an embodiment of a data system stand and a user position.

The various user input devices of the control panel 12 are oriented for use by an operator in an operator position. For example, rows of keys of a qwerty keyboard are oriented towards a front edge of the control panel 12 associated with an operator position adjacent or in front of that edge facing towards the data system 10 as shown in FIG. 2. The various user input devices may be positioned in a semi-circular orientation focused at the operator position for ergonomic use of the control panel by the operator.

The accessory or output device 16 comprises a video cassette recorder (VCR), color printer, black and white printer, tape recorder, compact disc reader or burner, facsimile machine, scanner, digital archiving devices, analog archiving devices, removable media devices, DVD, magneto optical drives or other optional equipment machine. As shown, the accessory device 16 comprises a rectilinear volume having four sides, a top and a bottom. Rounded, spherical or other shapes with a different number of sides may be used. A user interface or output port is provided on one side of the accessory device 16. For example, the user interface (e.g. buttons) for a printer or VCR are positioned on one or side face of the accessory device 16. As yet another example, output ports, such as a paper output of a printer or a tape door of a VCR, are provided on the side face of the accessory device 16.

The position of the accessory device 16 within the framework or housing of the data system stand 10 allows visual and physical access to the user interface or output port. For example, the user interface is positioned at an acute angle to the operator. The accessory device 16 is positioned to fit within an outer housing or the framework of the data system stand 10. In alternative embodiments, a portion, such as the side with the user interface or output port, extends from the framework or outer housing of the data system stand 10.

The data system 14 comprises one or more processors, application-specific integrated circuits or other components, such as a computer, workstation or ultrasound system. In one embodiment shown in FIGS. 1A–C, the data system 14 comprises a cube shaped housing oriented similar to a tower personal computer. Other arrangements of the data system 14 including one or more cards of electronics connected by wires or a back plane with or without a housing of any shape may be used. In one embodiment, output or input devices for use by an operator are provided on a front end of the data system 14 adjacent to an operator position, such as a floppy disk drive. Cabling connections are provided on a back end spaced away from an operator position.

The optional user tool mount 17 comprises one or more an electronic and/or physical connectors. In one embodiment, the user tool mount 17 includes a handle, hook, clip or other device for holding a user tool, such as a transducer probe, writing device, hand-held device, or other user tool. In an alternative embodiment, a plurality of releasable electrical and physical connectors for ultrasound transducers are provided. A plurality of hangers for holding the ultrasound probe adjacent to the respective transducer connector are also provided. The user tool mount 17 is positioned on the framework or housing of the data system stand 10 for visual and physical access by the user from an operator position.

The display 18 comprises a monitor, flat panel display, LCD or other display device. The display 18 is positioned above the control panel 12. The display 18 is positioned on a top of the stand 10, but other positions on a side or a corner of the stand 10 may be used. The front or view screen of the display 18 is oriented towards the operator position or towards the control panel 12. In one embodiment, the display 18 is rotatably mounted to the stand 10. Articulating or fixed mounts may also be used. In one embodiment, speakers are positioned adjacent to or connected with the display 18.

The casters 20 comprise three or more wheels or sets of wheels swivel connected to the bottom of the stand 10. In one embodiment, the stand 10 is movable by rolling on the casters 20. In alternative embodiments, the stand 10 is permanently fixed, uses tracks, wheels or other devices for moving. The casters 20 may be lockable so that the stand 10 may be used without movement.

The transformer 22 transforms electrical power input from a wall connection for use by the components of the stand 10. The transformer 22 electrically connects with the data system 14.

The components of the stand 10 are oriented for ergonomic use by the operator. Visual and physical access is provided to the control panel 12, user interface or output port 36 of the accessory device 16 and any user tool mounts 17. FIG. 2 shows the control panel 12 connected at about a 45° angle to the user interface 36 of the accessory device 16 and user tool mounts 17. As used herein, about includes within 3 degrees or other variation accounting for manufacturing tolerances. A centerline of the control panel 12 perpendicular to rows of keys 32 (i.e. extending from an operator 34 to the stand 10 or display 18) is at about a 45° angle to the user interface 36 of the accessory device 16 and the user tool mounts 17. Likewise, a tangent line to the front edge or a centerline of the control panel parallel to the rows of keys (i.e. extending parallel to the front of the operating facing the stand 10) is at about a 45° angle to the user interface 36 of the accessory device 16 and the user tool mounts 17.

In alternative embodiments, the angular relationship between the control panel 12 and the user interface 36 of the accessory device 16 or user tool mounts 17 relative to the operator position is 40°–50°. In yet other embodiments, a 30°–60° angular relationship is provided. In yet still further embodiments, a 10°–80° angular relationship is provided.

Various angles discussed herein are relative to an operator position. The operator 34 in FIG. 2 is shown in the operator position in front of the control panel 12 for viewing the display 18 in controlling the data system 14. From the operator position, the user 34 has access to the user interface 36 of the accessory device 16 and the tool mounts 17. A plane defined by the user interface 36 of the accessory device 16 intersects a centerline either perpendicular or parallel to centerlines in either the X or Y lateral dimensions of the control panel 12 where the operator position to the center of the stand is the X dimension at about 45°. Likewise, a plane associated with the connection of the user tool mounts 17 to the stand 10 intersects the X or Y centerline of the control panel 12 at about 45°.

Where the stand 10 has a generally rectangular configuration from a top view, the control panel 12 of one embodiment is connected at a corner 38 of the stand 10. A corner 38 is associated with the joining of two sides 40 and 42. The user interface 36 of the accessory device 16 is provided on one of the sides 42. Any user tool mounts 17 are provided on the other side 40. In alternative embodiments, the user tool mounts 17 are provided on the same side 42 as the user interface 36. In yet other alternative embodiments, the user interface 36 is on the other side 40, and the user tool mounts 17 is on the first side 42. In other embodiments, one or more user interfaces 36 are provided on a same side 42 or on different sides 40 and 42 as one or more other user interfaces.

From the operator's perspective while facing the stand 10 at the operator position, the operator has access to the user interface 36 on the left, the control panel 12 is provided at a center location, and the user tool mount 17 are provided on a right side or opposite side from the user interface 36 of the forward facing portion of the stand 10. The user interface 36 and user tool mount 17 are positioned slightly or much below the control panel 12. The display 18 is positioned on top of the stand 10 or above the control panel 12. In alternative embodiments, either one of the user interface 36 and user tool mount 17 are positioned on a same level or above the control panel 12.

Given the orientation of the various components as described above, objects surrounding the stand 10, such as a patient bed or a wall, do not obstruct access to a user interface 36 or user tool mount 17. The acute angle relationship of these components to the control panel 12 and the user position minimize the space used by the stand 12 while maximizing access for the operator. The operator's knees are also less likely to contact the user interface 36 or user tool mount 17 given the angle relationships. By positioning the user tool mount 17 just below, at or above the level of the control panel 12, tools associated with items hanging down such as cabling, avoid contact with the floor and prevent entanglement with the user's feet.

Figure 3A:
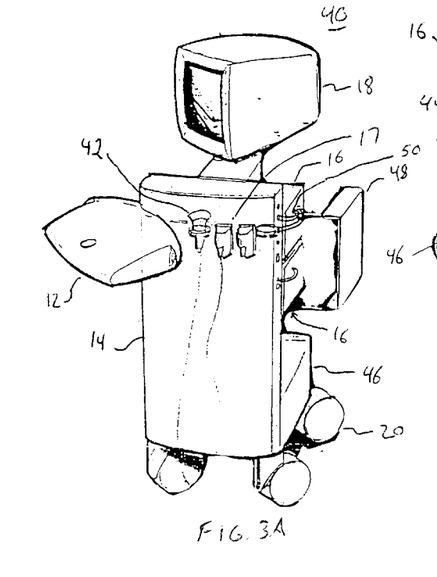
FIGS. 3A and 3B are right and left perspective views of the embodiment of the data system stand of FIG. 1A–C.
Figure 3B:
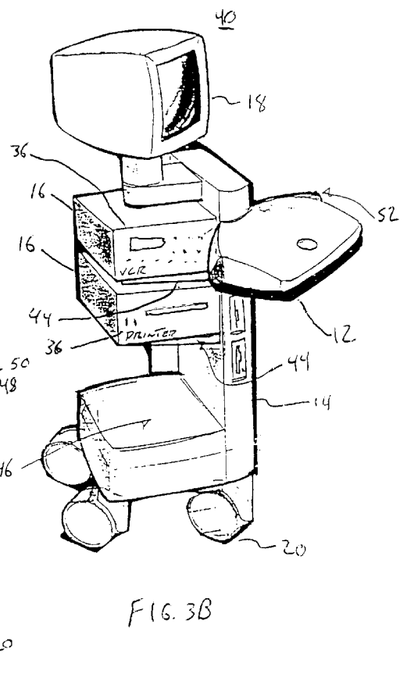

FIGS. 3A and 3B show right and left perspective views of an ultrasound data system stand 40 of an alternative embodiment. The ultrasound data system stand 40 includes various of the components oriented as discussed above in FIGS. 1A, 1B, 1C and 2. In this embodiment, the user tool mount 17 comprises transducer connectors and transducer hangers 42. As shown, three connectors and associated hangers 42 are provided, but fewer or more connectors and hangers 42 may be used. The transducer connectors 42 connect with the data system 14. The data system 14 comprises electronics for a medical diagnostic ultrasound system.

Shelves 44, such as brackets, arms, latches or other load bearing connections, support one or more accessory devices 16. The shelves 44 connect with the framework or outer housing of the data system 14. The accessory devices 16 are held onto the shelves 44 by a variety of mechanical means or may be placed on the shelves 44 without further connections. Some accessory devices 16 are built into the system stand 10, such as floppy drives, DVD drives, magneto optical devices or other accessory devices. The user interfaces or output ports 36 of the accessory devices 16 are shown on a left front side of the stand 10 relative to the user position adjacent to the control panel 12. On the opposite side of the stand, a plurality of cables 50 associated with the accessory devices 16 connect with the data system 14. In alternative embodiments, the cables 50 connect with the data system on the right side of the stand 40. A cable shield 48 connects over the cables 50 and a portion of the data system 14 to protect the cables 50. In one embodiment, the shield 48 releasably connects with the accessory devices 16 and/or the data system 14. As shown, the shield 48 is disconnected from the stand 40. The cable shield 48 comprises metal, plastic or other material.

A storage bin 46 is provided. The storage bin 46 comprises a drawer, an opened box, or other storage device. As shown, the storage bin 46 is positioned at a bottom of the stand 40 adjacent to the casters 20. In alternative embodiments, the storage 46 is positioned adjacent to, below or above the accessory devices 16. In yet other alternative embodiments, the electronics of the data system 14 are provided in the area shown comprising the storage bin 46.

Speakers 52 integrate onto the control panel 12. A speaker 52 is formed on each side of the control panel 12. In alternative embodiments, the speakers 52 are releasably attached to the control panel 12. In yet other alternative embodiments, the speakers 52 are positioned elsewhere on the stand 40.

Figure 4A:
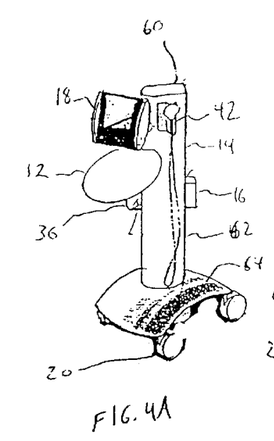
FIGS. 4A and 4B are right perspective views of two respective embodiments of ultrasound system stands.
Figure 4B:
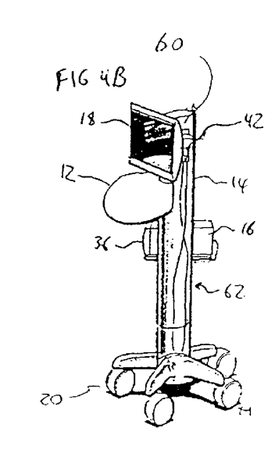

FIGS. 4A and 4B show an alternative embodiment of an ultrasound data system stand 60. The electronics of the ultrasound data system 14 are enclosed within the tower 62. Alternatively, part or all of the electronics of the data system 14 are included in a box or other structure connected to the tower 62 on a shelf or other connector. The accessory device 16 connects to the tower 62 on a shelf or with another latching structure. The accessory device 16 is oriented so that the control panel 12 is at an acute angle to the use interface 36 of the accessory device 16 relative to the position of an operator.

The transducer connector and associated hanger 42 connect on another side of the tower 62 than the user interface 36. In one embodiment, the transducer hanger integrates with the transducer connector. One or more hook or slotted shells are provided over the connector for hanging the transducer probe adjacent to the transducer connector.

The display 18 comprises a flat panel or LCD display connected to the front of the tower 62. In alternative embodiments, the display 18 connects to the top of the tower 62. As shown in FIG. 4B, five or more casters 20 are provided for additional stability. As shown in FIG. 4A, footrest plate 64 is provided.

Figures 5A, 5B, 5C, 8A:
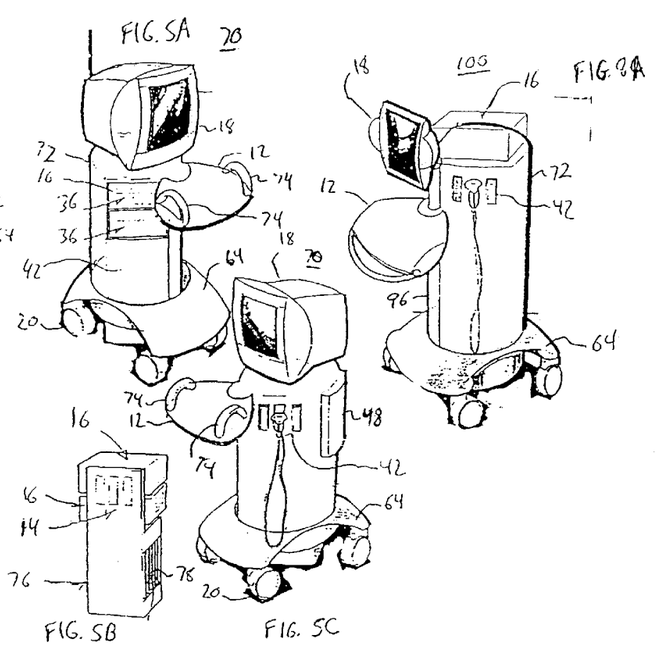
FIGS. 5A and 5C are left and right perspective views respectively of yet another embodiment of ultrasound system stand incorporating the ultrasound system shown FIG. 5B.
FIGS. 8A and 8B are perspective views of two other alternative embodiments of ultrasound system stands.

FIGS. 5A–C show another embodiment of an ultrasound system stand 70. An outer casing or housing 72 encloses the accessory devices 16 within the stand 70. The housing 72 is generally square from a top view, but may be circular or have other shapes. The user interfaces 36 of the accessory devices 16 are at an acute angle to the control panel 12 relative to an operator position. On a side of the casing 72 opposite the user interfaces 36, a cable shield or access plate 48 is provided. One or more handles 74 connect with the control panel 12 for guiding the stand 70 when moving the stand 70. A pocket or space, such as between the system base and system electronics, may be provided for slack transducer cable.

FIG. 5B shows a portion of the interior of the stand 70. An ultrasound data system 14 includes a back plane 76 and a plurality of cards and associated card slots 78. The accessory devices 16 connect with the back plane 76. Alternative arrangements with different positions of ultrasound electronics and associated cards and accessory devices 16 may be used, such as positioning the accessory devices 16 below or between card slots 78.

Figure 6:
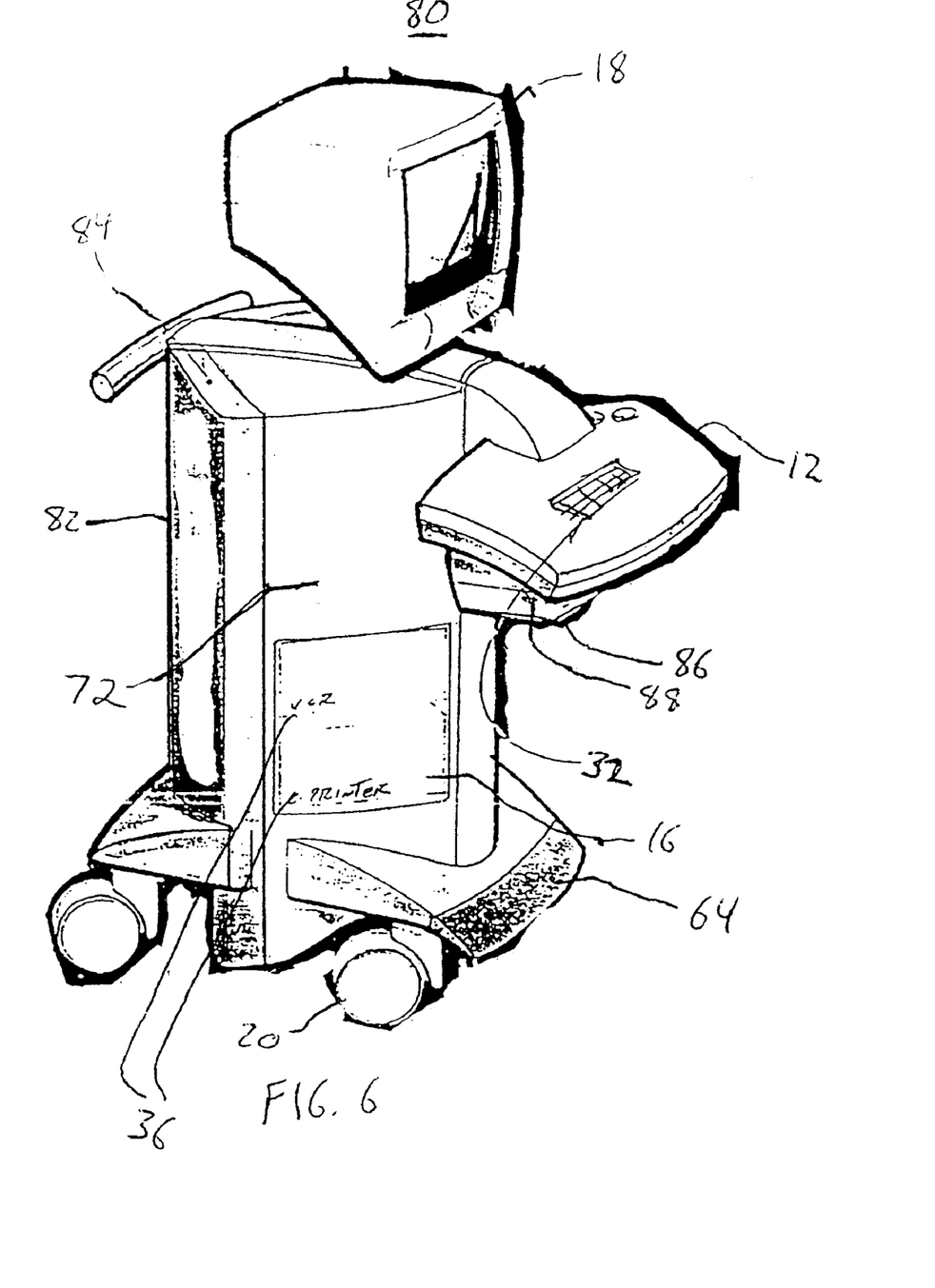
FIGS. 6 and 7 are two additional alternative embodiments of ultrasound system stands.

FIG. 6 shows another embodiment of an ultrasound data system stand 80. The user interfaces or output port 36 of the accessory devices 16 are exposed in the housing 72 below the control panel 12 near the bottom of the stand 80. The housing 72 also includes a housing extension 82. The housing extension 82 comprises plastic, metal or other material for providing additional space within the housing 72. For example, additional electronics associated with the data system 14 are housed within the panel extension 82. The panel extension 82 mounts to the housing 72. In alternative embodiments, the panel extension 82 comprises a door for allowing access within the housing 72.

A plastic or metal handle 84 is provided on a back corner of the stand 80 opposite the control panel 12. The handle 84 is used for moving the stand 80.

In one embodiment, one of the accessory devices 16 comprises a color printer. An additional black and white printer 86 is formed with or connects to the control panel 12. For example, the printer 86 is formed on the bottom of the control panel 12 with a paper output port 88 on a left or right side of the printer 86. In alternative embodiments, the printer 86 comprises a color printer, and a black and white, color or a different printer is provided as an accessory device 16.

Figures 7, 8B:
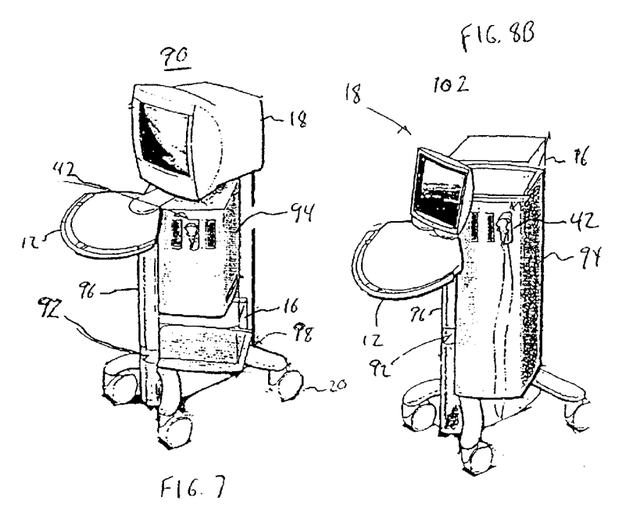

FIG. 7 shows yet another alternative embodiment of an ultrasound data system stand 90. A housing 94 covers part or all of the ultrasound data system. The housing 94 connects with a pillar 96. The pillar 96 and the housing 94 comprise plastic, metal, other material or combinations thereof. Trays or shelves 98 are provided for the accessory devices 16. One accessory device 16 is positioned outside of the housing 94. The pillar 96 includes a height adjustment section 92. The height adjustment section 92 comprises a pneumatic, spring loaded or other height adjustment device and associated activation lever for changing a height of the stand 90. The height of both the control panel 12 and the display 18 is adjusted at a same time. In alternative embodiments, a height adjustment is provided on just the control panel 12 or separately for each of the control panel 12 and the display 18.

FIGS. 8A and 8B show two additional embodiments of ultrasound data system stands 100 and 102. The stand 100 of FIG. 8A includes a housing 72 for the data system 14 with a pillar 96. The control panel 12 and the flat panel display 18 are releasably or adjustably connected to the pillar 96 for height adjustment. An activation lever, button, or other release device activates a pneumatic lift, spring lift, or electric motor. Alternatively, a hand powered screw jack is used. The housing 72 is adapted to hold or connect to an accessory device 16. The accessory device 16 rests on top of the stand 100 and housing 72. For the stand 102 of FIG. 8B, the housing 94 connects with the pillar 96 on an upper or a lower portion of the pillar above or below a height adjustment mechanism 92. The height adjustment mechanism 92 adjust the height of the control panel 12 and the flat panel display 18. The housing 94 is adapted to connect with or hold an accessory device 16 on the top of the housing 94.

Figure 9A:
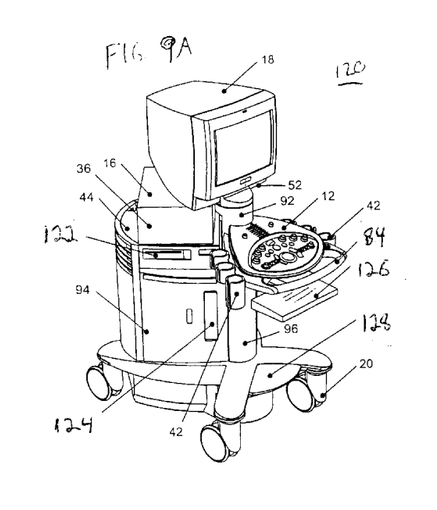
FIGS. 9A–D are perspective and top views of another alternative embodiment of an ultrasound system stand.
Figure 9B:
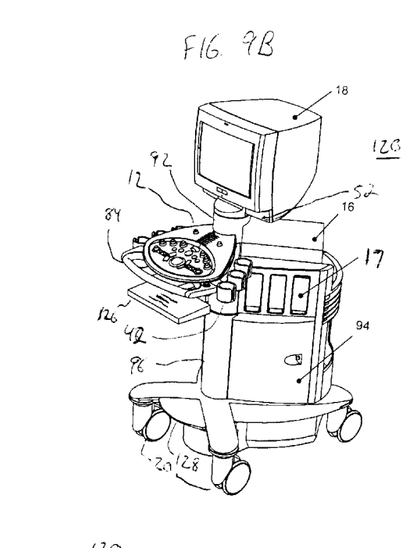
Figures 9C, 9D:
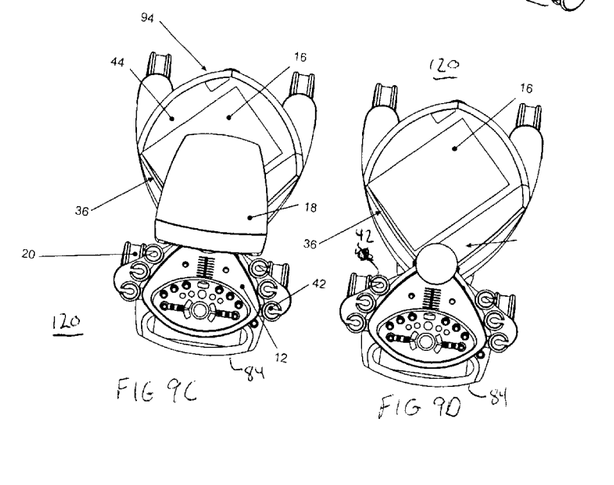

FIGS. 9A–D shows yet another embodiment of an ultrasound data system stand 120. FIG. 9C shows a top view of the stand 120, and FIG. 9D shows a top view without the display 18. One or more accessory devices 16 are mounted or rest on top of a shelf 44 on the top of the housing 94. The user interface 36 of the accessory device 16 is positioned at an acute angle to the user position as shown. Other accessory devices 16 are positioned within the housing 94 with the user interfaces 36 exposed on the same side as the user interface 36 of the accessory device 16 mounted on top of the housing 94. For example, a digital archive device 122 and physio connections (i.e., connectors for various electrical devices) 124 of one or more interface cards are provided.

The control panel 12 connects with the pillar 96. A height adjustment 92 allows use of the control panel 12 in a seated or standing position. A QWERTY keyboard 126 adjusts between a stowed position under the remainder of the control panel 12 and a use position extending from the remainder of the control panel 12. Transducer hangers 42 connect to one or both sides of the control panel 12. The handle 84 also connects with the control panel 12. Speakers 52 connect with the display 18 above the control panel 12.

A brake pedal 128 for locking or releasing the casters 20 is provided. The brake pedal 128 is positioned below the control panel 12 adjacent the pillar 96 for easy access by the operator.

Three user tool mounts 17, such as transducer connectors, are positioned on a side adjacent the pillar 96 and control panel 12 for easy access by the operator. The operator conveniently has access to the user interfaces 36, control panel 12 and user tool mounts 17. The user interfaces 36 and user tool mounts 17 are on adjoining but different sides of the stand 120 and are at acute angles to the user control panel axis extending from the operator position to the stand 120.

The embodiments discussed above for FIGS. 3–9 relate to ultrasound data systems. In alternative embodiments, other data systems as discussed above may be used. Accordingly, various components may be substituted for other components or not used, such as transducer connectors and hangers 42.

While the invention has been described above by reference to various embodiments, it should be understood that many changes and modifications can be made without departing from the scope of the invention. For example, various angles of the control panel 12 relative to the user interface of an accessory device or a user tool mount may be used. The housing of the various components of the stand may be flat, rounded, a framework, and of any material now known or later developed.

It is therefore intended that the foregoing detailed description be understood as an illustration of the presently preferred embodiment of the invention, and not as a definition of the invention. It is only the following claims, including all equivalents, that are intended to define the scope of this invention.

What is claimed is:

1. A moveable stand for operating a data system, the moveable stand comprising:
   a control panel mounted to the stand; and
   an accessory device having a user interface, the accessory device mounted to the stand;
   wherein the control panel is oriented at more than 10 degrees and less than 80 degrees to the user interface of the accessory device, the orientation relative to an operator position;
   wherein the stand comprises a rectilinear volume shape on at least two sides connected at a corner, the control panel extending from the corner of the stand and the accessory device incorporated within the stand such that the user interface is on a first of the at least two sides;
   further comprising a transducer connector on a second of the at least two sides, the user interface of the accessory device and transducer connectors on different sides of the control panel relative to the operator position.

2. The moveable stand of claim 1 wherein the control panel is oriented at more than 30 degrees and less than 60 degrees to the user interface of the accessory device.

3. The moveable stand of claim 1 wherein the control panel is oriented at more than 40 degrees and less than 50 degrees to the user interface of the accessory device.

4. The moveable stand of claim 1 wherein the control panel is oriented at about 45 degrees to the user interface of the accessory device.

5. The moveable stand of claim 1 wherein the control panel is oriented at more than 10 degrees and less than 80 degrees to any side of the accessory device, the accessory device comprising a generally rectilinear volume having four sides, a top and a bottom.

6. The moveable stand of claim 1 wherein the control panel comprises at least a keyboard, the operation position is facing the keyboard substantially perpendicular to rows of keys of the keyboard.

7. The moveable stand of claim 1 further comprising a display device positioned above the control panel wherein the accessory device is positioned below the control panel.

8. The moveable stand of claim 1 further comprising a user tool mount connected with the stand on a different side of the stand than the accessory device, the control panel oriented at more than 10 degrees and less than 80 degrees to the user tool mount, the orientation relative to an operator position.

9. The moveable stand of claim 1 wherein the accessory device comprises at least one of a printer and a video cassette recorder.

10. The moveable stand of claim 1 further comprising at least one caster connected with a bottom of the stand.

11. The moveable stand of claim 1 further comprising an ultrasound system within the moveable stand.

12. A stand for operating a data system, the stand comprising:
    a control panel connected with the stand; and
    an output device having an output port, the output device built into the stand;
    wherein the control panel is oriented at more than 10 degrees and less than 80 degrees to the output port, the orientation relative to an operator position;
    further comprising a transducer connector, the transducer connector on an exterior surface of the stand, the control panel in a center position with the output port of the output device and the transducer connector on opposite sides of the control panel from a user perspective.

13. The stand of claim 12 wherein the control panel is oriented at more than 40 degrees and less than 50 degrees to the user interface of the output device.

14. The stand of claim 12 wherein the control panel comprises at least a keyboard, the operation position is facing the keyboard substantially perpendicular to rows of keys of the keyboard; and
    further comprising a display device positioned above the control panel wherein the output device is positioned below the control panel.

15. The stand of claim 12 wherein the output device comprises at least one of a printer and a video cassette recorder.

16. The stand of claim 12 further comprising an ultrasound system connected with the stand.

17. An ultrasound system stand for use with an ultrasound system, the stand comprising:
    an ultrasound system connected with the stand;
    a control panel connected with the stand and operatively connected with the ultrasound system; and
    an accessory device having an user interface, the accessory device within the stand and operatively connected with the ultrasound system;
    wherein the control panel is oriented at more than 10 degrees and less than 80 degrees to the user interface of the accessory device, the orientation relative to an operator position;
    further comprising a transducer connector on the stand on a different side of the stand than the accessory device, the control panel oriented at more than 10 degrees and less than 80 degrees to the transducer connector, the orientation relative to an operator position, the transducer connector on an exterior surface of the stand, the control panel in a center position with the user interface of the accessory device and the transducer connector on opposite sides of the control panel from a user perspective.

18. The ultrasound system stand of claim 17 wherein the control panel is oriented at more than 30 degrees and less than 60 degrees to the user interface of the accessory device.

19. The ultrasound system stand of claim 17 wherein the control panel is oriented at more than 40 degrees and less than 50 degrees to the user interface of the accessory device.

20. The ultrasound system stand of claim 17 wherein the control panel is oriented at about 45 degrees to the user interface of the accessory device.

21. The ultrasound system stand of claim 17 wherein the control panel comprises at least a keyboard, the operation position is facing the keyboard substantially perpendicular to rows of keys of the keyboard.

22. The ultrasound system stand of claim 17 further comprising a display device positioned above the control panel wherein the accessory device is positioned below the control panel.

23. The ultrasound system stand of claim 17 further comprising transducer hanger connected with the stand on a same side of the stand as the transducer connector.

24. The ultrasound system stand of claim 17 wherein the stand comprises cube shape, the control panel extending from a corner of the stand, the accessory device incorporated within the stand, and the transducer connector on an exterior surface of the stand, the control panel in a center position with the user interface of the accessory device and the transducer connector on opposite sides of the control panel from a user perspective.

25. The ultrasound system stand of claim 17 wherein the accessory device comprises at least one of a printer and a video cassette recorder.

26. The ultrasound system stand of claim 17 further comprising at least one caster connected with a bottom of the stand.

27. A method for ergonomically connecting ultrasound system components, the method comprising the acts of:
   (a) mounting an accessory device within an ultrasound system stand, the accessory device having a user interface;
   (b) mounting a control panel to the ultrasound system stand;
   (c) orienting the control panel at more than 10 degrees and less than 80 degrees to the user interface of the accessory device relative to an operator position based on the mounting of (a) and (b);
   (d) connecting a transducer connector with the ultrasound system stand; and
   (e) orienting the control panel at more than 10 degrees and less than 80 degrees to the transducer connector relative to the operator position, the transducer connector spaced 90 to 270 degrees around the diameter of the ultrasound system stand from the user interface of the accessory device.

* * * * *